(12) United States Patent
Grant (10) Patent No.: US 11,900,467 B2
(45) Date of Patent: Feb. 13, 2024

(54) SELECTIVELY DETERMINING OPTIMAL COVERAGE

(71) Applicant: SelectQuote Insurance Services, Overland Park, KS (US)

(72) Inventor: Robert Clay Grant, Mission Hills, KS (US)

(73) Assignee: SelectQuote Insurance Services, Overland Park, KS (US)

( * ) Notice: Subject to any disclaimer, the term of this patent is extended or adjusted under 35 U.S.C. 154(b) by 58 days.

(21) Appl. No.: 17/078,925

(22) Filed: Oct. 23, 2020

(65) Prior Publication Data
US 2022/0129989 A1    Apr. 28, 2022

(51) Int. Cl.
| | |
|---|---|
| *G06Q 40/08* | (2012.01) |
| *G06Q 10/10* | (2023.01) |
| *G16H 10/20* | (2018.01) |
| *G16H 20/10* | (2018.01) |
| *G06Q 30/0204* | (2023.01) |
| *G06F 9/54* | (2006.01) |
| *G16H 40/20* | (2018.01) |
| *G06F 3/0482* | (2013.01) |
| *G06F 3/0483* | (2013.01) |

(52) U.S. Cl.
CPC ............ *G06Q 40/08* (2013.01); *G06F 9/547* (2013.01); *G06Q 10/10* (2013.01); *G06Q 30/0205* (2013.01); *G16H 10/20* (2018.01); *G16H 20/10* (2018.01); *G16H 40/20* (2018.01); *G06F 3/0482* (2013.01); *G06F 3/0483* (2013.01)

(58) Field of Classification Search
CPC .... G06Q 40/08; G06Q 10/10; G06Q 30/0205; G16H 40/20; G16H 20/10; G16H 10/20; G06F 9/547; G06F 3/0482; G06F 3/0483
USPC .................................................. 705/2–3, 2–4
See application file for complete search history.

(56) References Cited

U.S. PATENT DOCUMENTS

| | | | | |
|---|---|---|---|---|
| 2012/0253829 | A1* | 10/2012 | John | G16H 40/67 705/2 |
| 2013/0054258 | A1* | 2/2013 | Cohan | G06Q 30/0639 705/2 |
| 2014/0039911 | A1* | 2/2014 | Iyer | G06Q 30/0207 705/2 |
| 2014/0144674 | A1* | 5/2014 | Sarraf | C25D 17/005 174/250 |
| 2016/0225096 | A1* | 8/2016 | Wells | G06Q 10/10 |
| 2018/0075212 | A1* | 3/2018 | Kubey | G06Q 10/087 |
| 2021/0065862 | A1* | 3/2021 | Siegel | G16H 40/63 |

* cited by examiner

*Primary Examiner* — Joy Chng
(74) *Attorney, Agent, or Firm* — Erise IP, P.A.

(57) ABSTRACT

Systems and methods are disclosed for identifying a set of suitable coverage plans for a healthcare consumer. A starting coverage year and geographical location are received. The healthcare consumer is presented with an option to provide a list of prescription medicines as well as an option to provide an identification of one or more pharmacies and one or more preferred physicians. The healthcare consumer is presented with a user interface component for creating an account. A list of plans is presented based on the one or more geographical location parameters, the list of prescription medicines, and pharmacies, and the identification of one or more preferred physicians.

20 Claims, 9 Drawing Sheets

SELECTIVELY DETERMINING OPTIMAL COVERAGE

TECHNICAL FIELD

Embodiments of the invention generally relate to determining an optimal health insurance coverage package based on medical needs of a healthcare consumer. Regulated insurance coverage options have a vast array of interacting parameters so that it is difficult for a healthcare consumer to manually determine what would be an optimal coverage package to select.

SUMMARY

Embodiments of the invention address this problem by automatically calculating optimal coverage package parameters and identifying a set of suitable coverage plans for a healthcare consumer. In particular, in a first embodiment, the invention includes one or more non-transitory computer-readable media storing computer-executable instructions that, when executed by a processor, perform a method for identifying a set of suitable coverage plans for a healthcare consumer, the method comprising: receiving a coverage year corresponding to a year on which coverage should begin, receiving one or more geographical location parameters, presenting the healthcare consumer with an option to provide a list of prescription medicines required by the healthcare consumer, presenting the healthcare consumer with an option to provide an identification of one or more pharmacies from which the healthcare consumer receives at least one medicine in the list of prescription medicines, presenting the healthcare consumer with an option to provide an identification of one or more preferred physicians, presenting the healthcare consumer with a user interface component for creating an account, determining one or more plans based on at least one of: the one or more geographical location parameters; the list of prescription medicines required by the healthcare consumer; the one or more pharmacies from which the healthcare consumer receives at least one medicine in the list of prescription medicines, and the identification of one or more preferred physicians, and presenting the user with a menu corresponding to the one or more plans.

In a second embodiment, the invention includes a method for identifying a set of suitable coverage plans for a healthcare consumer, the method comprising: receiving a coverage year corresponding to a year on which coverage should begin, receiving one or more geographical location parameters, presenting the healthcare consumer with an option to provide a list of prescription medicines required by the healthcare consumer, presenting the healthcare consumer with an option to provide an identification of one or more pharmacies from which the healthcare consumer receives at least one medicine in the list of prescription medicines, presenting the healthcare consumer with an option to provide an identification of one or more preferred physicians, presenting the healthcare consumer with a user interface component for creating an account, determining one or more plans based on at least one of: the one or more geographical location parameters, the list of prescription medicines required by the healthcare consumer, the one or more pharmacies from which the healthcare consumer receives at least one medicine in the list of prescription medicines, and the identification of one or more preferred physicians, presenting the user with a menu corresponding to the one or more plans, receiving a plan selection from the healthcare consumer, and enrolling the healthcare consumer in the selected plan.

In a third embodiment, the invention includes a system comprising at least one processor and at least one non-transitory memory storing computer executable instructions that when executed by the processor cause the system to carry out actions comprising: receiving a coverage year corresponding to a year on which coverage should begin, receiving one or more geographical location parameters, presenting a healthcare consumer with an option to provide a list of prescription medicines required by the healthcare consumer, presenting the healthcare consumer with an option to provide an identification of one or more pharmacies from which the healthcare consumer receives at least one medicine in the list of prescription medicines, presenting the healthcare consumer with an option to provide an identification of one or more preferred physicians, determining one or more plans based on at least one of: the one or more geographical location parameters, the list of prescription medicines required by the healthcare consumer, the one or more pharmacies from which the healthcare consumer receives at least one medicine in the list of prescription medicines, and the identification of one or more preferred physicians, presenting the user with a menu corresponding to the one or more plans, receiving a plan selection from the healthcare consumer, and enrolling the healthcare consumer in the selected plan.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

The drawing figures do not limit the invention to the specific embodiments disclosed and described herein. The drawings are not necessarily to scale, emphasis instead being placed upon clearly illustrating the principles of the invention.

DETAILED DESCRIPTION

The subject matter of the invention is described in detail below to meet statutory requirements; however, the description itself is not intended to limit the scope of claims. Rather, the claimed subject matter might be embodied in other ways to include different steps or combinations of steps similar to the ones described in this document, in conjunction with other present or future technologies. Minor variations from the description below will be understood by one skilled in the art and are intended to be captured within the scope of the claimed invention. Terms should not be interpreted as implying any particular ordering of various steps described unless the order of individual steps is explicitly described.

The following detailed description of embodiments of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of embodiments of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate reference to "one embodiment" "an embodiment", or "embodiments" in this description do not necessarily refer to the same embodiment and are also not mutually exclusive unless so stated and/or except as will be readily apparent to those skilled in the art from the description. For example, a feature, structure, or act described in one embodiment may also be included in other embodiments but is not necessarily included. Thus, the technology can include a variety of combinations and/or integrations of the embodiments described herein.

Operational Environment for Embodiments of the Invention

Figure 1:
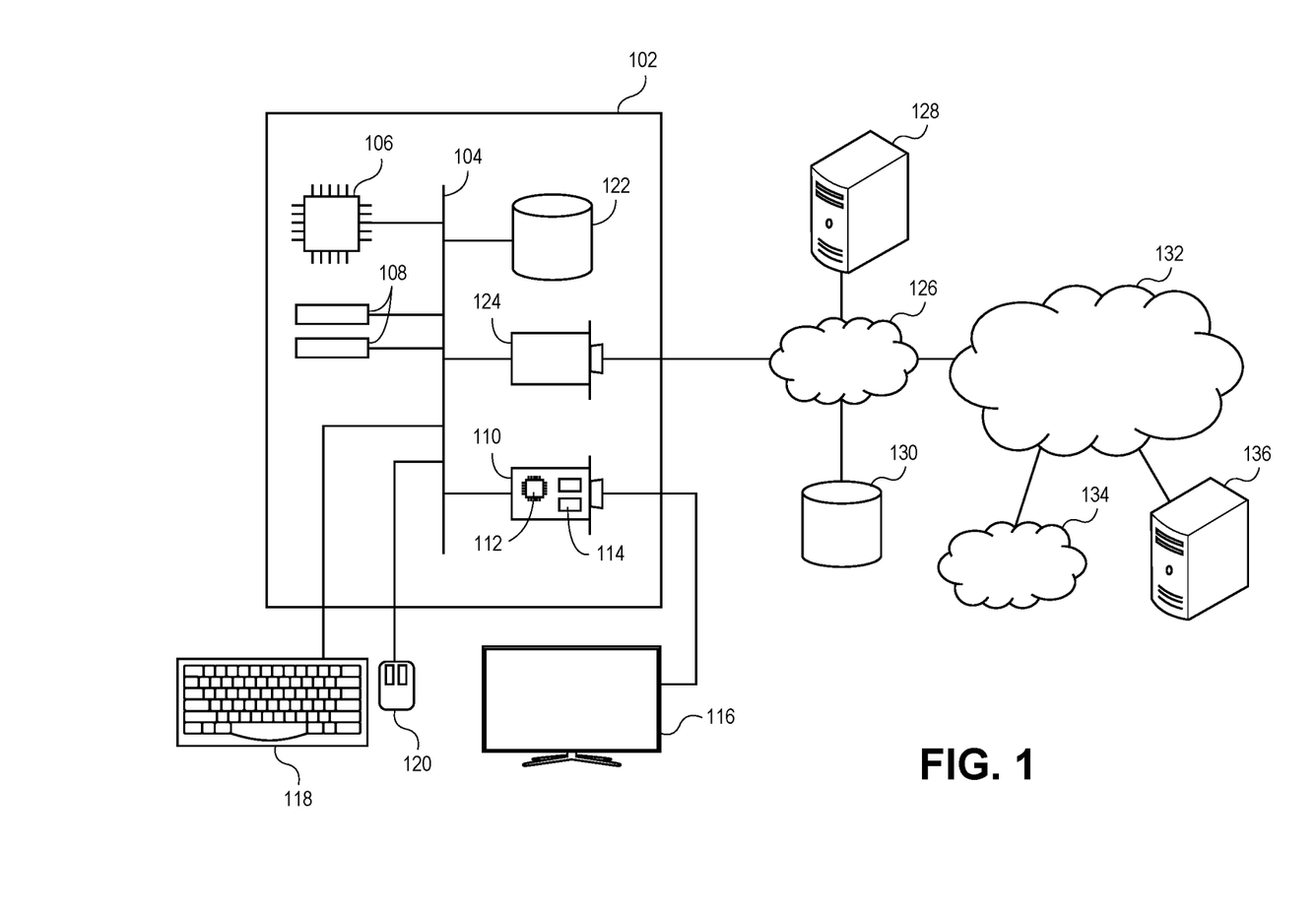
FIG. 1 depicts an exemplary hardware platform for certain embodiments of the invention.

Turning first to FIG. 1, an exemplary hardware platform for certain embodiments of the invention is depicted. Computer 102 can be a desktop computer, a laptop computer, a server computer, a mobile device such as a smartphone or tablet, or any other form factor of general- or special-purpose computing device. Depicted with computer 102 are several components, for illustrative purposes. In some embodiments, certain components may be arranged differently or absent. Additional components may also be present. Included in computer 102 is system bus 104, via which other components of computer 102 can communicate with each other. In certain embodiments, there may be multiple busses or components may communicate with each other directly. Connected to system bus 104 is central processing unit (CPU) 106. Also attached to system bus 104 are one or more random-access memory (RAM) modules 108. Also attached to system bus 104 is graphics card 110. In some embodiments, graphics card 110 may not be a physically separate card, but rather may be integrated into the motherboard or the CPU 106. In some embodiments, graphics card 110 has a separate graphics-processing unit (GPU) 112, which can be used for graphics processing or for general purpose computing (GPGPU). Also, on graphics card 110 is GPU memory 114. Connected (directly or indirectly) to graphics card 110 is display 116 for user interaction. In some embodiments no display is present, while in others it is integrated into computer 102. Similarly, peripherals such as keyboard 118 and mouse 120 are connected to system bus 104. Like display 116, these peripherals may be integrated into computer 102 or absent. Also connected to system bus 104 is local storage 122, which may be any form of computer-readable media and may be internally installed in computer 102 or externally and removably attached.

Computer-readable media include both volatile and non-volatile media, removable and nonremovable media, and contemplate media readable by a database. For example, computer-readable media include (but are not limited to) RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data temporarily or permanently. However, unless explicitly specified otherwise, the term "computer-readable media" should not be construed to include physical, but transitory, forms of signal transmission such as radio broadcasts, electrical signals through a wire, or light pulses through a fiber-optic cable. Examples of stored information include computer-useable instructions, data structures, program modules, and other data representations.

Finally, network interface card (NIC) 124 is also attached to system bus 104 and allows computer 102 to communicate over a network such as network 126. NIC 124 can be any form of network interface known in the art, such as Ethernet, ATM, fiber, Bluetooth, or Wi-Fi (i.e., the Institute of Electrical and Electronics Engineers (IEEE) 802.11 family of standards). NIC 124 connects computer 102 to local network 126, which may also include one or more other computers, such as computer 128, and network storage, such as data store 130. Generally, a data store such as data store 130 may be any repository from which information can be stored and retrieved as needed. Examples of data stores include relational or object oriented databases, spreadsheets, file systems, flat files, directory services such as LDAP and Active Directory, or email storage systems. A data store may be accessible via a complex API (such as, for example, Structured Query Language), a simple API providing only read, write and seek operations, or any level of complexity in between. Some data stores may additionally provide management functions for data sets stored therein such as backup or versioning. Data stores can be local to a single computer such as computer 128, accessible on a local network such as local network 126, or remotely accessible over public Internet 132. Local network 126 is in turn connected to public Internet 132, which connects many networks such as local network 126, remote network 134 or directly attached computers such as computer 136. In some embodiments, computer 102 can itself be directly connected to public Internet 132.

Figure 2:
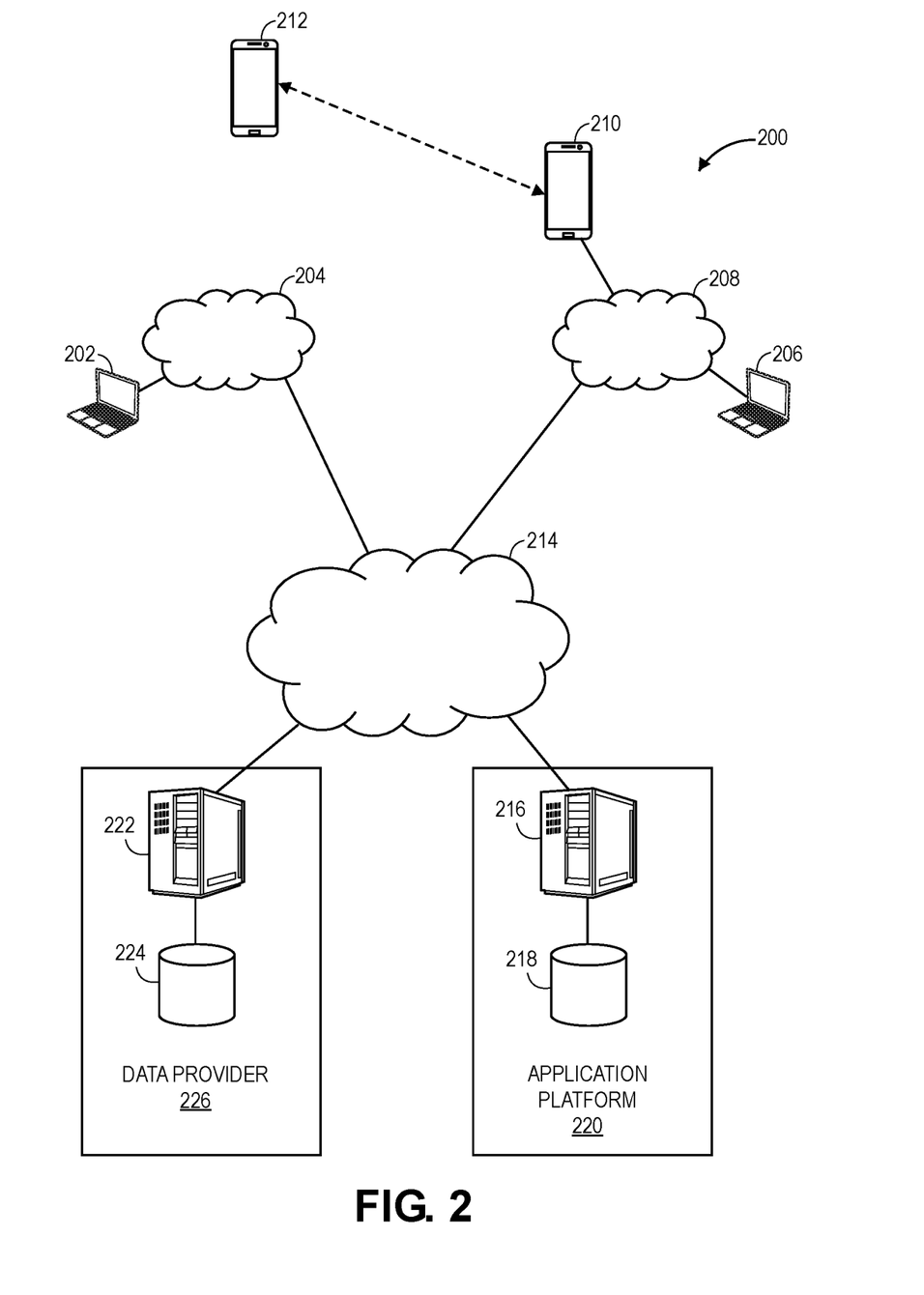
FIG. 2 depicts components of a system for carrying out embodiments of the invention.

Turning now to FIG. 2, an exemplary diagram illustrating components of a system for carrying out embodiments of the invention is depicted and referred to generally by reference numeral 200. System 200 provides a mechanism for identifying a set of suitable coverage plans for a healthcare consumer. In one embodiment, system 200 is used to enable the health care consumer to choose a coverage plan using an agent. In this embodiment, the consumer calls the agent at agent telephony device 210 using consumer telephony device 212 over a telephony network. Agent telephony device 210 and the consumer may be connected via voice over IP, for example. Telephony devices 210 and 212 may also be landline telephony devices or any kind of a mobile telephone, such as a cellular mobile device.

In this embodiment, the agent uses agent device 206 to access and interact with various applications and associated data items within system 200. Agent device 206 may be any form of computing device described above with respect to FIG. 1. For example, agent device 206 may be a desktop computer, laptop computer, tablet computer, or smartphone. Agent device 206 may access components of system 200 by way of agent local network 208. Agent local network 208 may be any kind of a wired or wireless data network, such as Ethernet as defined by any of the IEEE 802.3 family of standards, Wi-Fi as defined by the IEEE 802.11 family, or any mobile data network standard.

In various other embodiments, a healthcare consumer interacts directly with various applications and associated data items within system 200. In some embodiments the healthcare consumer interacts directly with consumer device 202, which may likewise be any form of computing device described above with respect to FIG. 1. By contrast with agent device 206, consumer device 202 is used directly by the healthcare consumer, who for the purposes of illustration may provide medical parameters regarding desired healthcare coverage and directly select and enroll in a healthcare plan. Consumer device 202 may access components of system 200 by way of consumer local network 204. Like agent local network 208, consumer local network 204 may be any kind of a wired or wireless data network as described above.

Web server server 216 provides a front-end and user interface for application platform 220 in system 200. For example, web server 216 may present a web interface with which users of application platform 220 interact with healthcare plan lists and other content stored in application platform repository 218. Users of system 200 may use devices such as agent device 206 or consumer device 202 to interact with other elements of system 200 via a web browser associated with devices 202 and 206. Alternatively, or in addition, web server 216 may provide a direct client/server interface with which a user may use devices such as consumer device 202 to interact with elements of system 200 via dedicated software. For example, if consumer device 202 is a smartphone, the dedicated software may be in the form of a smartphone app. As yet another alternative, the user may use dedicated software in consumer device 202 to interact with other components of system 200, where the dedicated software interacts with web server 216 via the web interface of web server 216 or a web services application programming interface (API) associated with web server 216. Generally speaking, and as described in greater detail below, platform repository 218 stores data associated with application platform 220. As depicted, web server 216 is directly connected to platform repository 218. However, in various embodiments, platform repository 218 may be connected via a network such as network 214. For example, platform repository 218 may be implanted as network-attached storage (NAS) or cloud storage.

In some embodiments, data provider server 222 provides a web services interface for data provider 226 in system 200. For example, data provider 226 may present a web services API in connection with which consumers of data provider 226 interact with data stored in data provider repository 224. Users of system 200 may use devices such as consumer device 202 to interact directly with data provider server 222.

In alternative embodiments, web server 216 communicates with data provider server 222 to obtain information from data provider 226 and integrate the information from data provider 226 with other application information in application platform 220. As depicted, data provider server 222 is directly connected to data provider repository 224. However, in various embodiments, data provider repository 224 may be connected via a network such as network 214. For example, data provider repository 224 may be NAS or cloud storage.

The components of system 200 may be interconnected via network 214. For example, network 214 may be public Internet 132 as described in connection with FIG. 1. Alternatively, some or all of the components of system 200 may be interconnected via a local area network (LAN), wide area network, or virtual private network (VPN), which may in turn interconnect to other elements of the system via public Internet 132. In some embodiments, consumer device 202 and agent device 206 connect to application platform 220 over a public Internet.

Operation of Embodiments of the Invention

Figure 3:
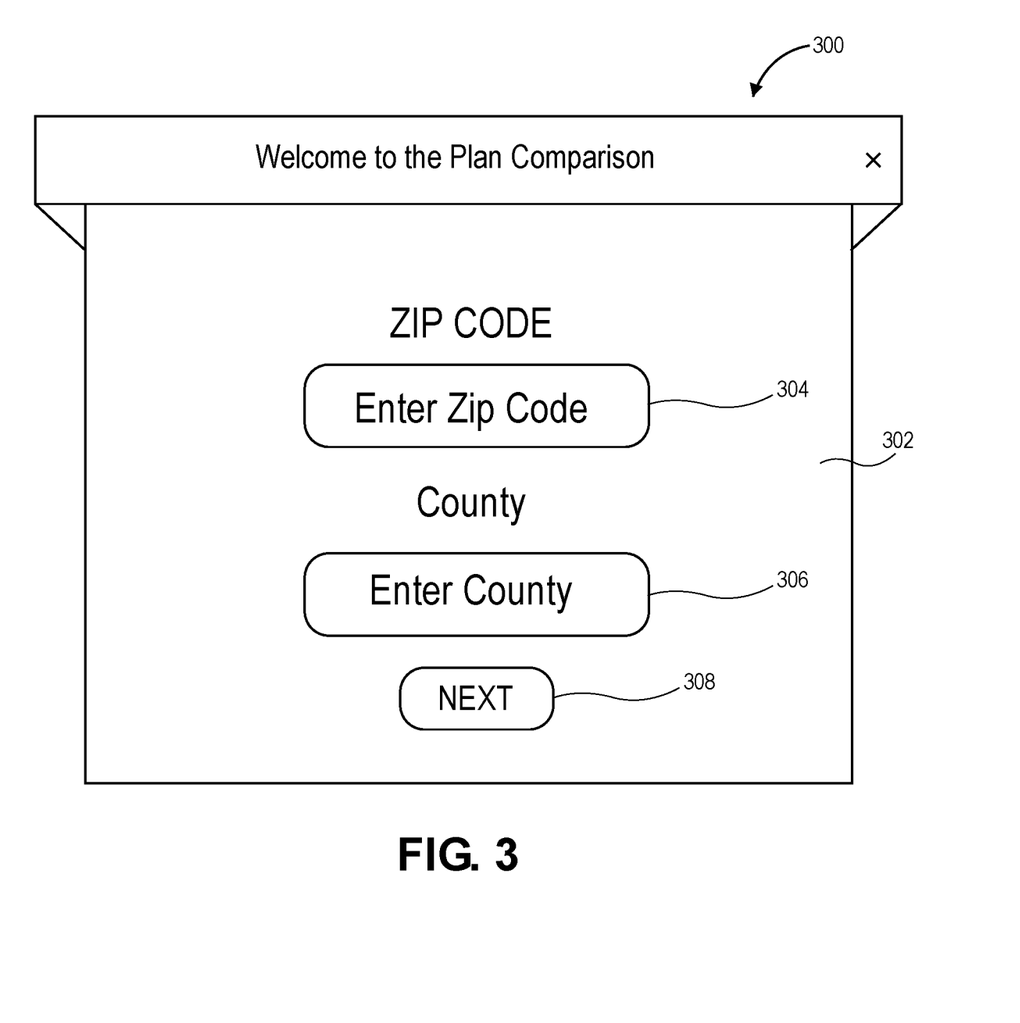
FIG. 3 depicts an exemplary user interface component for receiving geographical location parameters.

FIG. 3 depicts an exemplary user interface component 300 for receiving geographical location parameters. In some embodiments, the least amount of information a healthcare consumer can provide to receive insurance quotes is a ZIP code and a county. In some embodiments, available insurance coverage plans are offered based on the healthcare consumer's geographical location parameters, such as ZIP code and county of residence. In some embodiments, rating areas are defined by county, metropolitan statistical area, or group of ZIP codes. In some embodiments, all households within a particular rating area will have the same available rates for a particular coverage plan depending on the rating area prices for a particular plan may be higher lower than other ratings areas. In some embodiments, insurance coverage and particular plans may only be offered in certain ratings areas.

In one embodiment, modal dialog 302 is provided into which the health care consumer can input certain geographical location parameters. In some embodiments, this modal dialog is provided in connection with a web application running on a server such as web server 216 that is accessed using a laptop or mobile device such as consumer device 202 as described in connection with FIG. 1 above. In one embodiment, numeric text box input 304 is provided into which a healthcare consumer can input a ZIP code associated with the healthcare consumer's residence. In this embodiment, the healthcare consumer is additionally required to input a county of residence into alphanumeric text box input 306. In some embodiments, depending on whether the ZIP code or county is entered first, the contents of the remaining text box input will autocomplete or provide a list of possible entries in a drop-down list. For example, if ZIP code 94303 were input into numeric text box input 304, the two possible counties will be presented as possible options in alphanumeric text box input 306, specifically "San Mateo County," and "Santa Clara County." In some embodiments, until a valid ZIP code and county are selected, next button 308 will be inactive. In these embodiments, once a user has selected a valid ZIP code and county, next button 308 will become active, and the user can click next button 308 and advance to a next step in the application.

Figure 4:
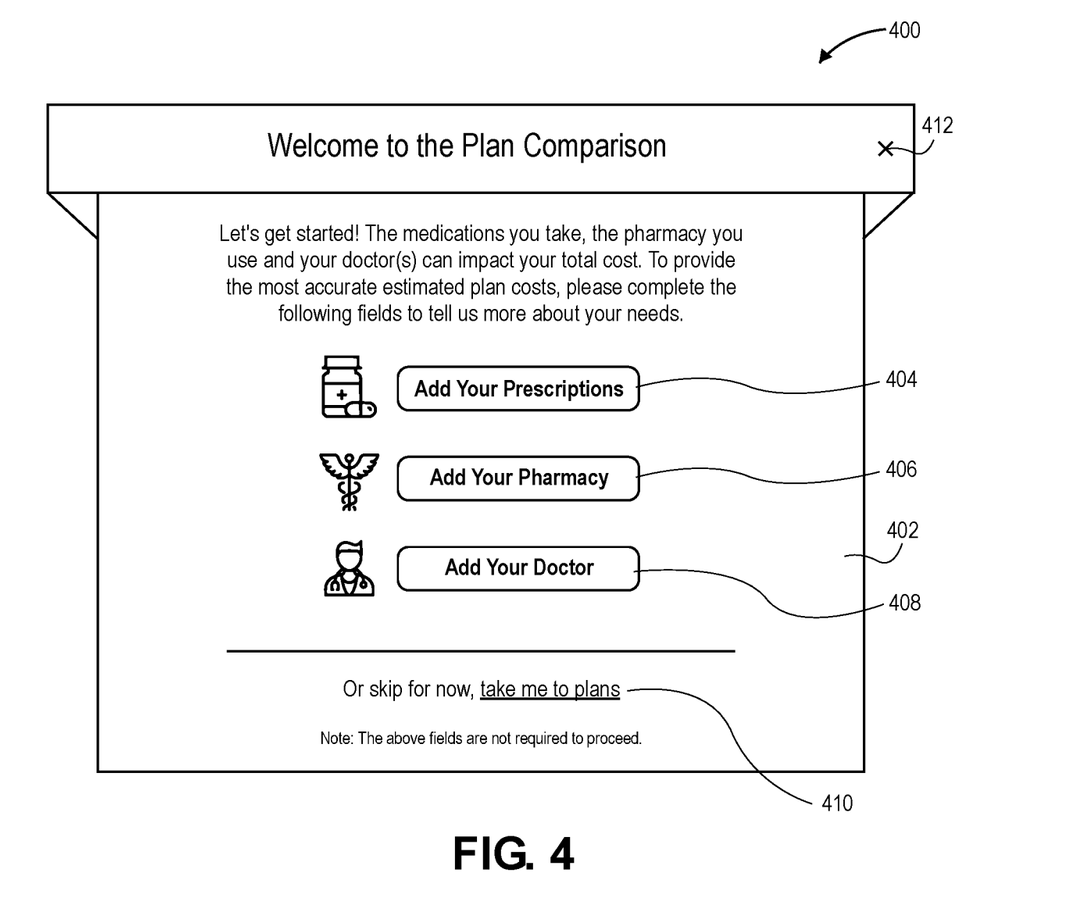
FIG. 4 depicts an exemplary user interface component for receiving a request to provide an identification of prescriptions, one or more pharmacies and a preferred doctor or doctors.

FIG. 4 depicts an exemplary user interface component 400 for receiving a request to provide medical parameters such as an identification of prescriptions, one or more pharmacies, and preferred health care providers for a particular healthcare consumer. In some embodiments, the prescription medications taken by a consumer, the pharmacy used by the consumer and the doctor or other healthcare provider preferred by the consumer may impact the consumer's total cost for a healthcare plan. In some embodiments, users are prompted to complete certain fields associated with relevant medical parameters in order to provide the consumer with optimal plans and the most accurate estimated plan costs.

In some embodiments, a healthcare consumer is not required to provide any medical parameters in order to be provided with a list of healthcare plans. Since the systems described herein may be used by healthcare consumers, insurance agents, or other representatives of a healthcare consumer, the term "user" is employed below to represent the user who is using the system on behalf of the healthcare consumer. Accordingly, the user may be the healthcare consumer or the healthcare consumer's agent or representative. In some embodiments, the user is provided notification that the healthcare consumer is not required to provide any health-related information that is not used to determine enrollment eligibility. In this case, the user can simply click on a link such as link 410, entitled "take me to plans," and the user will be taken to a list of plans such as the list provided in connection with FIG. 7 below. If, however, the user chooses to provide some medical parameters, the user may choose to do so in connection with modal dialog 402.

In these embodiments, the consumer may click on button 404, entitled "Add Your Prescriptions," which will allow the user to navigate to a user interface component that will allow the user to input a list of prescription medications, such as the user interface component described in connection with FIG. 5 below. Alternatively, the consumer may click on button 406, entitled "Add Your Pharmacy," which will allow the user to input one or more pharmacies. In some embodiments, a location of the user's device is obtained from geolocating components contained within the user's device and possible pharmacies are suggested to the user based on geographical proximity or other factors such as cost-related factors. The user may also click on button 408, entitled "Add Your Doctor," which will allow the user to navigate to a user interface component that will allow the user to input one or more preferred healthcare providers, such as the user interface component described in connection with FIG. 6 below. In some embodiments, clicking exit button 412 closes modal dialog box 402 and takes the user to a plan list (such as the plan list of FIG. 7) based on the current amount of information collected from the user at the time exit button 412 is clicked.

Figure 5:
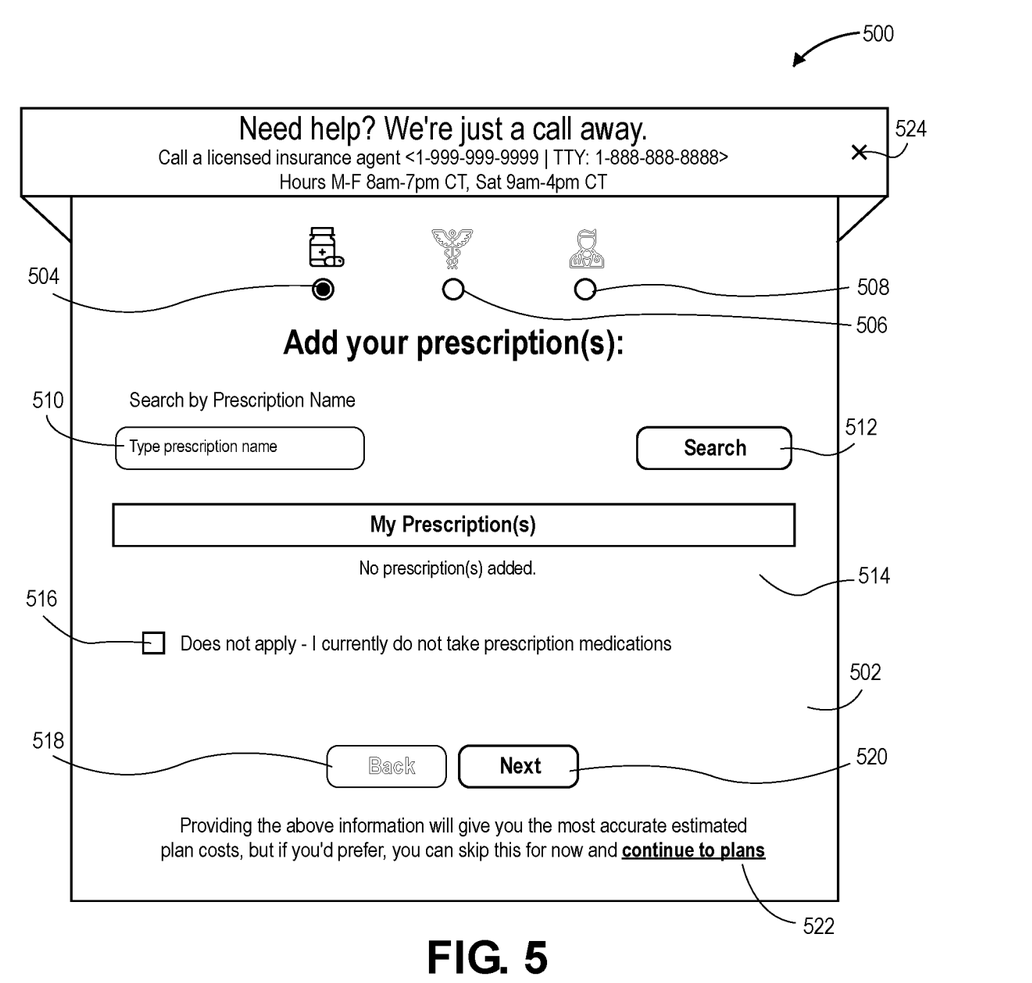
FIG. 5 depicts an exemplary user interface component for receiving a list of prescriptions.

FIG. 5 depicts an exemplary user interface component 500 for receiving a list of prescriptions. In various embodiments, although radio button 504 for adding prescriptions is selected, other options (radio buttons 506 and 508) to provide medical parameters are dynamic, meaning the consumer can choose medical parameters in any order desired by the consumer. As the user completes each section, the user may be guided to a next section that remains uncompleted. In some, cases the user may choose to proceed in order from left to right (radio button 504, 506, and 508 respectively).

In some embodiments, the user may begin typing a prescription name into text box 510. In various embodiments, the application autocompletes known prescription names based on a formulary accessed, e.g., via web services in connection with a data provider such as data provider 226 of FIG. 2. Once the user has typed the name of a prescription or part of the name of a prescription, the user may click search button 512 to search various formularies for a prescription. Once the user finds a prescription that the consumer needs, the user can click on that prescription to add it to the list of prescriptions 514 displayed in modal dialog box 502. The user may click checkbox 516, if the consumer currently does not have any prescriptions. In some embodiments, a stack of medical parameter inputs is maintained in state associated with the presently described software application, and if the user wishes to return to the modal dialog box previously visited, the user may click back button 518 and the user will be navigated to the modal dialog box previously occurring on the stack. Alternatively, if the user decides to advance to the next screen, the user may click "Next" button 520, and the current screen will be pushed onto the stack.

When the user is finished inputting medical parameters, the user can simply click on link 522, entitled "continue to plans," and the user will be taken to a list of plans such as the list provided in connection with FIG. 7 below. Moreover, clicking exit button 524 closes modal dialog box 502 and takes the user to a plan list (such as the plan list of FIG. 7) based on the current amount of information collected from the user at the time exit button 524 is clicked.

Figure 6:
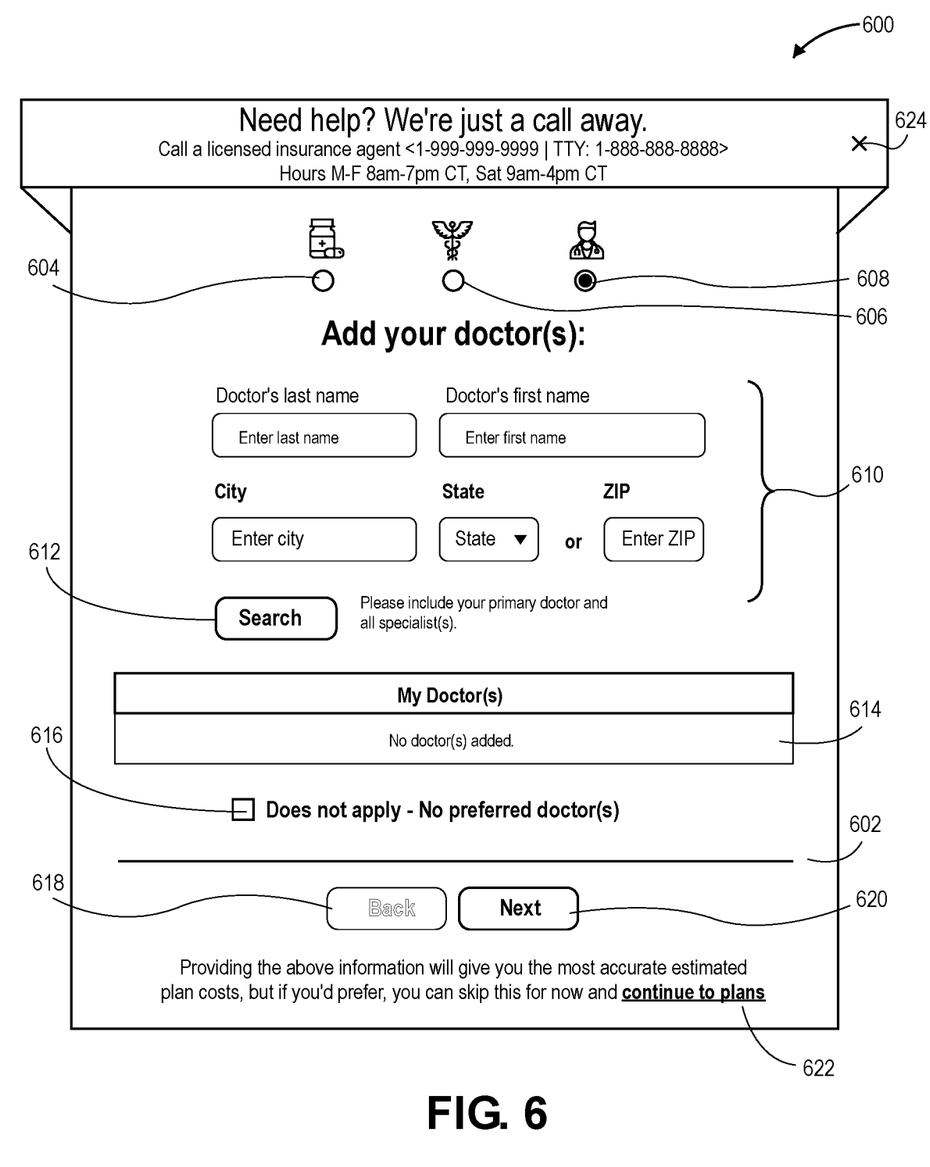
FIG. 6 depicts an exemplary user interface component for receiving an identification of one or more preferred healthcare providers.

FIG. 6 depicts an exemplary user interface component 600 for receiving an identification of one or more preferred healthcare providers. In various embodiments, although radio button 608 for adding preferred physicians is selected, other options (radio buttons 604 and 606) to provide other medical parameters are dynamic, meaning the user can choose to input medical parameters in any order desired by the user. As the user completes each section, the user may be guided to a next section that remains uncompleted. In some, cases the user may choose to proceed in order from left to right (radio button 604, 606, and 608 respectively).

In some embodiments, the user may begin typing a doctor's first or last name into input fields 610. In various embodiments, the application autocompletes known doctors' names based on a directory of healthcare providers accessed, e.g., via web services in connection with a data provider such as data provider 226 of FIG. 2. Once the user has typed the name or part of the name or address of a healthcare provider, the user may click search button 612 to search various directories for a healthcare provider. Once the user finds a healthcare provider that the user wants to select, the user can click on that provider to add the provider to the list of providers 614 displayed in modal dialog box 602. The user may click checkbox 616, if the user currently does not have any preferred healthcare provider. In some embodiments, a stack of medical parameter inputs is maintained in state associated with the presently described software application, and if the user wishes to return to the modal dialog box previously visited, the user may click back button 618 and the user will be navigated to the modal dialog box previously occurring on the stack. Alternatively, if the user decides to advance to the next screen, the user may click "Next" button 620.

When the user is finished inputting medical parameters, the user can simply click on link 622, entitled "continue to plans," and the user will be taken to a list of plans such as the list provided in connection with FIG. 7 below. Moreover, clicking exit button 624 closes modal dialog box 602 and takes the user to a plan list (such as the plan list of FIG. 7) based on the current amount of information collected from the user at the time exit button 624 is clicked.

Figure 7:
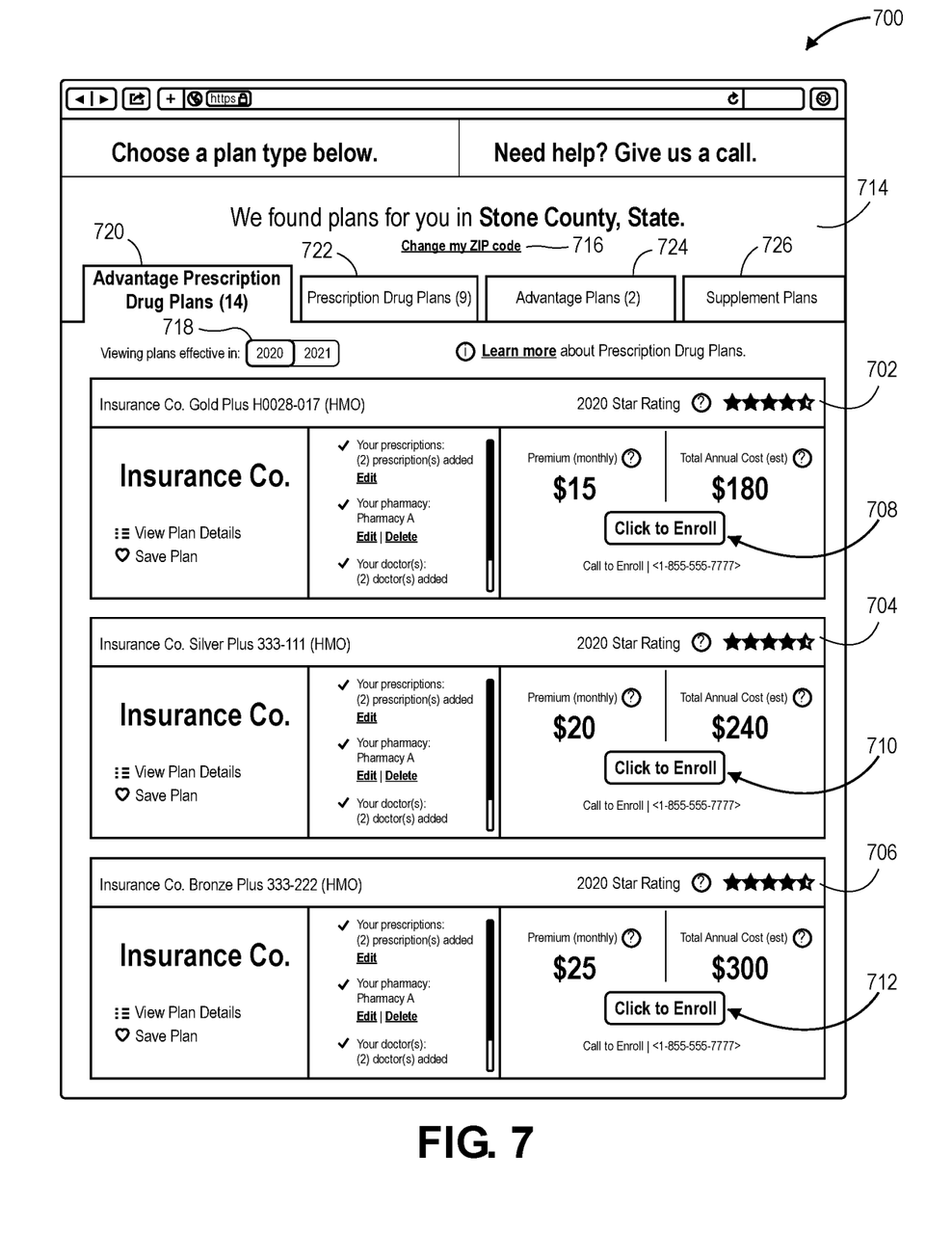
FIG. 7 depicts an exemplary user interface for providing a menu of insurance plan choices.

FIG. 7 depicts an exemplary user interface 700 for providing a menu of insurance plan choices. The menu of insurance plan choices may also be called a plan wall. As noted in connection with FIG. 3, the minimum information needed to receive a list of plans is a ZIP code and county. Additionally, availability of plans and pricing is impacted by geographical region. Therefore, the ZIP code and county are presented in region 714. If the user desires to change the ZIP code and/or county, the user may click link 716, entitled "Change my ZIP code." In some embodiments, the user may also click on the county to change the county and ZIP code. In some embodiments, the plan wall is dynamically updated when the geographical location changes. In certain embodiments, the updated plan information is obtained dynamically by a web services call to a data provider such as data provider 226 of FIG. 2.

In some embodiments, the plan wall is broken up into various tabs such as tab 720, entitled "Advantage Prescription Drug Plans," tab 722, entitled "Prescription Drug Plans," tab 724, entitled "Advantage Plans," and tab 726, entitled "Supplement Plans". The user may select a different list of plans by clicking one of tabs 720, 722, 724, and 726. The user may select a different plan year by clicking plan year selector 718. Once the plan wall is displayed, different plans are laid out and plan line items such as plan line item 702, lion line item 704, and plan line item 706. The user can choose to enroll in a particular plan by clicking one of the "Click to enroll" buttons 708, 710 and 712 respectively.

Figure 8:
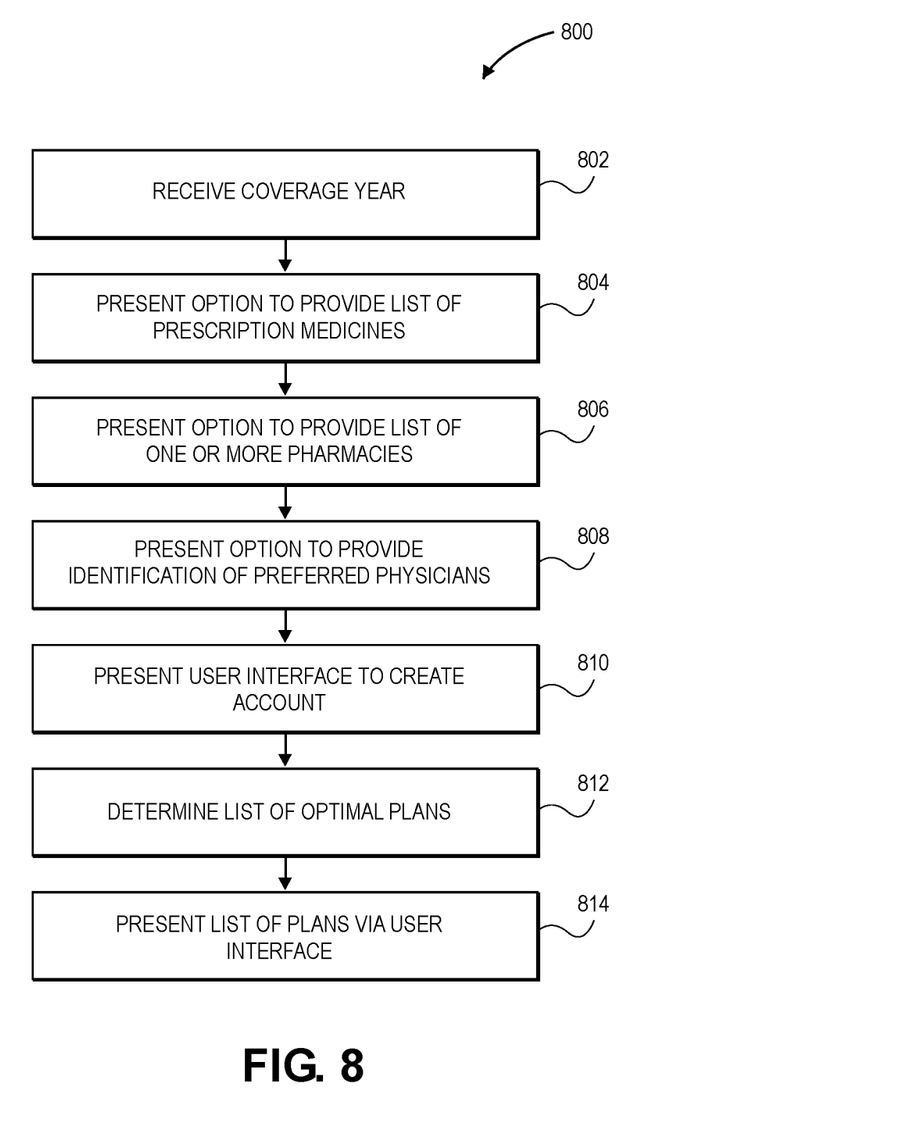
FIG. 8 depicts an exemplary flowchart illustrating the operation of a method in accordance with one embodiment of the invention.

FIG. 8 depicts an exemplary flowchart 800 illustrating the operation of a method in accordance with one embodiment of the invention. In some embodiments, the exemplary method is carried out by an application such as a web application running on web server 216 of FIG. 2. At step 802, the application provides a user interface component for receiving a desired plan coverage year. In some embodiments, the plan coverage year may include the current year and the next year. In some embodiments, the available coverage years depend on a residential geographical region of a healthcare consumer. In some embodiments, the application receives only actually available plan coverage years at this step. In some embodiments, only actually available coverage years are presented to a user for possible selection.

At step 804, the application presents an option to provide a list of prescription medicines. In some embodiments, the user may begin typing a prescription name into a text box, and the application autocompletes known prescription names based on a formulary accessed, e.g., via web services in connection with a data provider such as data provider 226 of FIG. 2. Once the user has typed the name of a prescription or part of the name of a prescription, the user may click a search button to search various formularies for a prescription. Once the user finds a prescription that the consumer needs, the user can click on that prescription to add it to a list of prescriptions displayed by the application. The user may click a checkbox if the consumer currently does not have any prescriptions.

At step 806, the application presents an option to provide a list of one or more pharmacies. In some embodiments, a location of the user's device is obtained from geolocating components contained within the user's device and possible pharmacies are suggested to the user based on geographical proximity or other factors. In some embodiments, all known pharmacies within a certain geographic radius are suggested. In other embodiments, only those pharmacies are suggested that are associated with plans that are available to the healthcare consumer or those pharmacies that have prescriptions having a lowest cost based on the prescription medicines already input by the user.

At step 808, the application presents an option to provide an identification of preferred physicians or other healthcare providers. In some embodiments, the user may begin typing a doctor's first or last name into input fields. In various embodiments, the application autocompletes known doctors' names based on a directory of healthcare providers accessed, e.g., via web services in connection with a data provider such as data provider 226 of FIG. 2. Once the user has typed the name or part of the name or address of a healthcare provider, the user may click a search button to search various directories for a healthcare provider. Once the user finds a healthcare provider that the user wants to select, the user can click on that provider to add the provider to the list of providers displayed by the application. The user may click a checkbox if the user currently does not have any preferred health care provider At step 810, the application presents a user interface to create an account. In some embodiments, the user may create an account in the application platform and save the information that the user has input up to that point. In some embodiments, the user's account name will be the user's email address or the healthcare consumer's email address. Alternatively, the user will provide an email address as part of the enrollment process. In these embodiments, a confirmation email will be sent to one or more of the email addresses confirming creation of the account and optionally providing a link to return to the plan application process. At step 812, the application determines a list of optimal healthcare plans. In some embodiments, the optimal plan will have an overall lowest cost based both on the monthly or yearly cost of the plan as well as other costs such as expected cost of prescription medicines and doctor visits. At step 814, the application presents the list of plans via a graphical user interface, which is also known as a plan wall.

Figure 9:
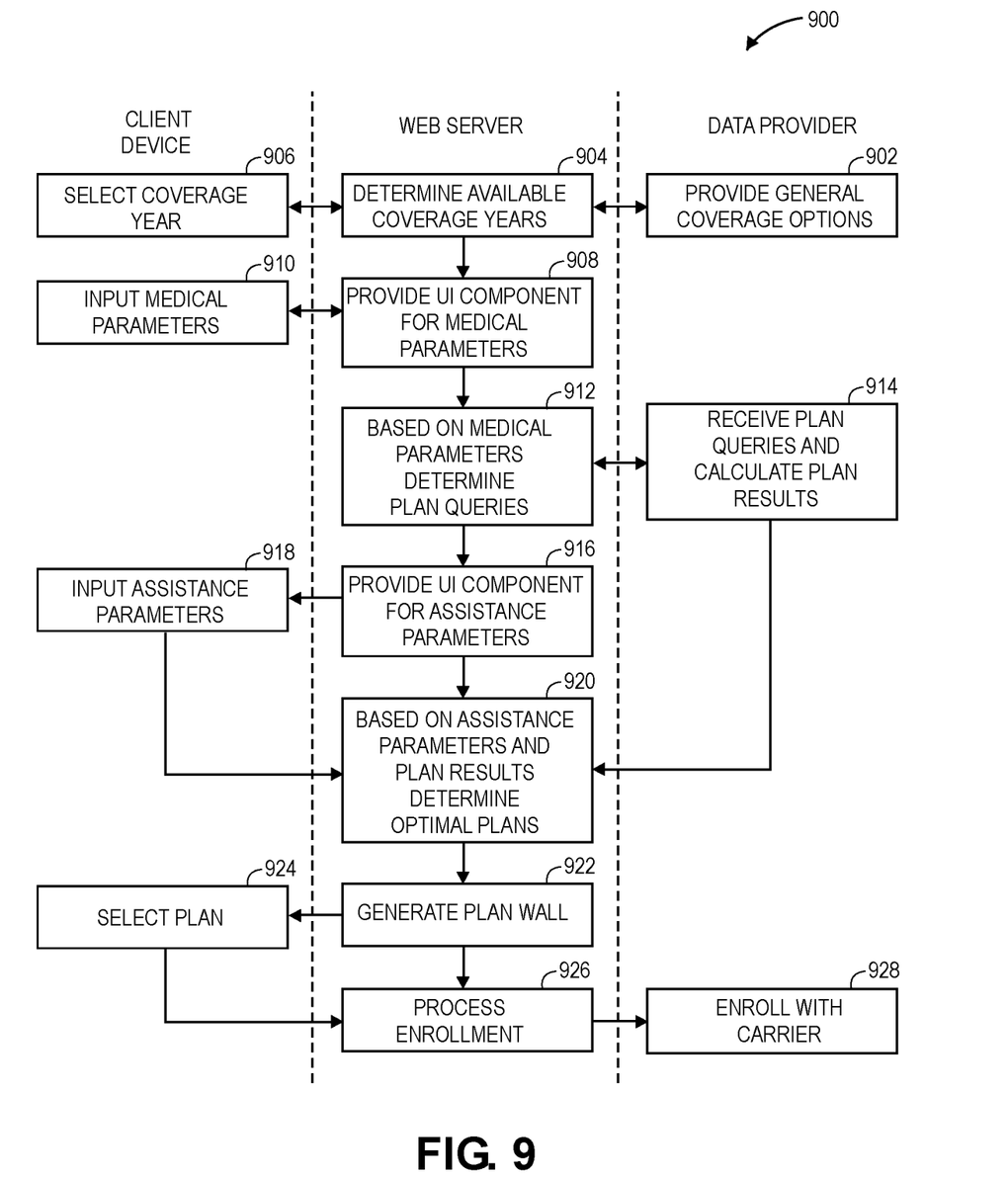
FIG. 9 depicts an exemplary swim lane diagram for illustrating the operation of a method in accordance with one embodiment of the invention.

FIG. 9 depicts an exemplary swim lane diagram illustrating the operation of a method in accordance with one embodiment of the invention. The swim lane diagram is referred to generally by reference numeral 900. The process begins at step 902 with the provision of general coverage options. In some embodiments, a data provider such as data provider 226 of FIG. 2 provides general coverage options for a particular geographical region. In some embodiments, this information is obtained by way of a web services call to the data provider.

At step 904, the web server that is hosting the application determines available coverage years. In some embodiments, the web server may be web server 216 of FIG. 2 in the context of application platform 220. In these embodiments, the available coverage years will be the current year and the following year, however certain coverages may depend on geographical location such as residential ZIP code and county and certain other characteristics of the healthcare consumer. In some embodiments, once the web server has determined which coverage years are available, the web server may render a selectable user interface component and present the option to select a coverage year so that a user of application platform 220 may select a coverage year. At step 906, this selectable user interface component is rendered at the client device and the user selects a coverage year.

At step 908, the web server provides a user interface component for receiving medical parameters. In some embodiments, the medical parameters include a list of prescription medications that a healthcare consumer has currently prescribed to the healthcare consumer. The medical parameters may also include one or more preferred pharmacies that the healthcare consumer uses to obtain the healthcare consumer's prescription medicines. The medical parameters may also include an identification of one or more preferred healthcare providers such as doctors, nurses, physician assistants, or nurse practitioners. In some embodiments, the user interface component for obtaining this information may be analogous to the user interface components described in connection with FIGS. 3-6 above. In some embodiments, in order to provide autocomplete functionality and to ensure that only available selections are actually input by the user, the web server may make web service calls to certain data providers that provide information about the various medical parameters to be input by the user. In some embodiments, the data providers may be data provider 226 as described in connection with FIG. 2 above. At step 910, this user interface component is rendered on a client device and a user of the client device inputs medical parameters using the client device user interface.

At step 912, the web server utilizes the input medical parameters to formulate plan queries. In some embodiments, the plan queries may consider a geographical region in which the particular healthcare consumer resides. The plan queries may also be selected to seek out possible alternative pharmacies for which certain medical prescriptions may be less expensive under certain plans. The plan queries may also be selected to seek out possible alternative prescription medicines, which may be less expensive under certain plans. In some embodiments, the plan queries include queries directed to identifying generic pharmaceuticals that may be less expensive than a corresponding name-brand pharmaceutical. Plan queries may also seek out alternative pharmaceuticals that have the same or similar therapeutic effect. The plan queries may also be selected to seek out possible alternative healthcare providers which may be less expensive for the healthcare consumer under certain plans. The plan queries may be transmitted to one or more data providers.

At step 914, one or more data providers receive the above-formulated plan queries. In some embodiments, the plan queries are executed by the data provider against the data provider's internal or external data sources. As noted above, the plan queries may include a request to identify a generic pharmaceutical or an alternate pharmaceutical. In this situation, the data provider will query its data sources based on the plan query to identify possible generic or alternate medicines. Alternatively, the data provider will check the prices for certain prescription medicines at various pharmacies that may be provided in the received plan queries. In this way, the plan queries are executed by the data provider to result in calculated plan results.

Next, or in parallel, at step 916, the web server provides a user interface component to receive assistance parameters from the healthcare consumer. In some cases, a health care consumer may be entitled to special assistance in paying for or subsidizing a healthcare plan. Some consumers may not be eligible for special assistance by virtue of their income or other characteristics such as wealth or other financial resources. Other consumers may be eligible for programs such as Medicare or Medicaid or a dual full subsidy for both. Some consumers may receive full or partial financial assistance. The user interface component may provide a percentage numerical text box to receive a numerical percentage of assistance or the user interface component may provide a dropdown menu containing certain percentages such as 0%, 25%, 50%, 75% or 100% corresponding to the percentage of financial assistance to which the healthcare consumer is entitled. In some embodiments, this percentage is used later in this figure to calculate certain costs associated with the list of plans presented to the user.

At step 918, the user inputs assistance parameters. If the user knows the answer to the consumer's assistance parameters, the user inputs an appropriate value. Alternatively, if the user does not know the answer, the user indicates that the user does not know, for example by clicking a check box corresponding to "unknown." At any point in the process the user may create an account in the application platform and save the information that the user has input. In some embodiments, the user's account name will be the user's email address or the healthcare consumer's email address. Alternatively, the user will provide an email address as part of the enrollment process. In these embodiments, a confirmation email will be sent to one or more of the email addresses confirming creation of the account and optionally providing a link to return to the plan application process.

At step 920, the web server determines a list of optimal healthcare plans for the healthcare consumer based upon the assistance parameters and plan results calculated at step 914. In some embodiments, this list of healthcare plans may be based on alternate pharmaceuticals, pharmacies, or healthcare providers. In alternative embodiments, the plans may be based on the consumer's preferences input by the user. In yet other embodiments, when, for example, the user has only input geographical information, the plan options for that geographical region will be displayed with costs adjusted for any assistance parameters input by the user.

At step 922, based on the list of optimal plans determined at step 920, the web server generates a plan wall user interface component and presents it to the user at the user's client device. In some embodiments, the plan wall contains plan details which can be accessed by clicking on one of the plans in the plan wall. In some embodiments, the plan details are updated dynamically based on information obtained by a particular plan carrier by, for example making a web services call to a data provider having information about particular plans. The data provider may be the carrier itself or another data provider. In some embodiments, if the user has not provided enough information to determine an optimal list of plans, before presenting the user with a plan wall, the application presents the user with a user interface component that informs the user that if the user provides additional information a more optimal list of plans could be provided. In some embodiments, this user interface component models various scenarios to illustrate to the user that if the user would input additional information, the user could have access to a more optimal list of plans. In some embodiments, the sections that need to be completed are updated dynamically such that only sections that have not been completed are displayed. The user may then navigate back to the user interface by which the user may input additional medical parameters. Next, the user selects a plan (step 924) by, for example, clicking a button to enroll in the selected plan.

At step 926, the web server processes enrollment of the healthcare consumer into the selected plan. In some embodiments, this entails receiving personal information from the user such as the user's name, date of birth, gender, and email address. The user may elect to review a summary of benefits associated with the plan. In some embodiments, the benefits summary may be presented in multiple languages. The user may also access evidence of coverage, which is a document that describes in detail the benefits of the plan. The evidence of coverage may be provided in multiple languages. In some embodiments, if the user has not input information regarding financial assistance, an additional "Extra Help Alert" is provided after the user clicks to enroll. In this situation the user is alerted that the healthcare consumer may be eligible for financial assistance. In some embodiments, the web server uses available information about the healthcare consumer to estimate a likelihood that the healthcare consumer would be eligible for financial assistance and alerts the user that the consumer may be eligible. In some embodiments, the user is notified that the healthcare consumer should speak to an insurance agent or other enrollment specialist to determine whether the consumer is eligible for financial assistance. In some embodiments, the web server automatically processes enrollment with a carrier through a carrier back end system. In alternative embodiments, the user is directed to a carrier application platform so that the user can perform enrollment directly into an insurance carrier system. In some embodiments, a transition modal dialog or other user interface component is presented to the user before redirecting the user to the insurance carrier's application platform. At step 926, an insurance carrier carries out enrollment of the healthcare consumer into the healthcare consumer's selected plan.

Many different arrangements of the various components depicted, as well as components not shown, are possible without departing from the scope of the claims below. Embodiments of the invention have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims. Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. One or more non-transitory computer-readable media comprising computer-executable instructions that, when executed by at least one processor, perform a method of providing healthcare plan choices, the method comprising:
   causing a first modal dialog to be provided for display on a user interface component, the first modal dialog comprising a first prompt, the first prompt requesting one or more geographical location parameters;
   responsive to receiving the one or more geographical location parameters, causing a second modal dialog to be provided for display on the user interface component, the second modal dialog comprising a second prompt and a bypass button, the second prompt presenting a user with an option of providing one or more medical parameters or selecting the bypass button operable to bypass the option of providing of the one or more medical parameters;
   wherein the second prompt further comprises an add your pharmacy button and an add your doctor button;
   receiving, by the second modal dialog and from the user, the one or more medical parameters;
   wherein the one or more medical parameters comprise a plan wall;
   updating the plan wall based on a county and a zip code by a web services call to a data provider;
   wherein the plan wall comprises one or more tabs;
   the one or more tabs comprising options including: advantage prescription drug plans, prescription drug plans, advantage plans, and supplement plans;
   causing display of the plan wall;
   receiving at least one selection from the options;
   determining one or more healthcare plan choices based at least in part on the one or more geographical location parameters and the at least one selection from the options and causing a menu to be provided for display on the user interface component, the menu comprising the one or more healthcare plan choices;
   determining pharmacies in an area associated with the one or more geographical location parameters;
   filtering the pharmacies to only those that provide the one or more medical parameters;
   causing display of a list of the pharmacies that provide the one or more medical parameters within the area;
   receiving, by the user interface component and from the user, input of at least one preferred pharmacy that is not on the list of the pharmacies because the at least one preferred pharmacy provides alternative medications that have a similar therapeutic effect; and
   adding the at least one preferred pharmacy to the list of the pharmacies.

2. The one or more non-transitory computer-readable media of claim 1, wherein the one or more geographical location parameters comprises the zip code and the county.

3. The one or more non-transitory computer-readable media of claim 1, wherein the menu comprises a navigate-back button operable to allow the user to navigate back to the second modal dialog, and wherein the method further comprises:
   responsive to receiving an indication of the navigate-back button having been selected, causing the second modal dialog to be again provided for display on the user interface component; and
   responsive to receiving the one or more medical parameters, determining again the one or more healthcare plan choices based at least in part on the one or more medical parameters, and causing the menu to be again provided for display on the user interface component, the menu comprising the one or more healthcare plan choices as having been determined again based at least in part on the one or more medical parameters.

4. The one or more non-transitory computer-readable media of claim 3, wherein the one or more medical parameters comprises an identification of one or more prescription medicines, and wherein determining the one or more healthcare plan choices comprises:
   identifying a pharmacy having a minimum total cost for the one or more prescription medicines and determining the one or more healthcare plan choices based at least in part on the pharmacy having the minimum total cost for the one or more prescription medicines.

5. The one or more non-transitory computer-readable media of claim 4, wherein the one or more medical parameters comprises a further identification of one or more preferred pharmacies, and wherein the pharmacy having the minimum total cost for the one or more prescription medicines differs from the one or more preferred pharmacies.

6. The one or more non-transitory computer-readable media of claim 5, wherein identifying the pharmacy having the minimum total cost for the one or more prescription medicines comprises making an application programming interface call to a pharmaceutical cost data provider.

7. The one or more non-transitory computer-readable media of claim 5, wherein the one or more prescription medicines comprises a first medicine that has at least one generic alternative, and wherein the minimum total cost is based at least in part on the at least one generic alternative.

8. A method of providing healthcare plan choices to a user, the method comprising:

causing a first modal dialog to be provided for display on a user interface component, the first modal dialog comprising a first prompt, the first prompt requesting one or more geographical location parameters;

responsive to receiving the one or more geographical location parameters, causing a second modal dialog to be provided for display on the user interface component, the second modal dialog comprising a second prompt and a bypass button, the second prompt presenting the user with an option of providing one or more medical parameters or selecting the bypass button operable to bypass the option of providing of the one or more medical parameters;

wherein the second prompt further comprises an add your pharmacy button and an add your doctor button;

wherein the one or more medical parameters comprise a plan wall;

updating the plan wall based on a county and a zip code by a web services call to a data provider;

wherein the plan wall comprises one or more tabs, the one or more tabs comprising options including: advantage prescription drug plans, prescription drug plans, advantage plans, and supplement plans;

causing display of the plan wall;

receiving at least one selection of the options;

responsive to receiving an indication of the bypass button having been selected, determining a plurality of healthcare plan choices based at least in part on the one or more geographical location parameters and the at least one selection from the options and causing a menu to be provided for display on the user interface component, the menu comprising the plurality of healthcare plan choices and for respective ones of the plurality of healthcare plan choices, a plan selection button operable to allow the user to select a corresponding one of the plurality of healthcare plan choices;

responsive to receiving a further indication of a respective plan selection button having been selected, causing a third modal dialog to be provided for display on the user interface component, the third modal dialog comprising information for enrolling in a respective one of the plurality of healthcare plan choices corresponding to the respective plan selection button;

determining pharmacies in an area associated with the one or more geographical location parameters;

filtering the pharmacies to only those that provide the one or more medical parameters;

causing display of a list of the pharmacies that provide the one or more medical parameters within the area;

receiving, by the user interface component and from the user, input of at least one preferred pharmacy that is not on the list of the pharmacies; and adding the at least one preferred pharmacy to the list of the pharmacies.

9. The method of claim 8, wherein the one or more geographical location parameters comprises the zip code and the county.

10. The method of claim 8, wherein the menu comprises a navigate-back button operable to allow the user to navigate back to the second modal dialog, and wherein the method comprises:

responsive to receiving an additional indication of the navigate-back button having been selected from the menu, causing the second modal dialog to be again provided for display on the user interface component; and responsive to receiving the one or more medical parameters, determining again the plurality of healthcare plan choices based at least in part on the one or more medical parameters, and causing the menu to be again provided for display on the user interface component, the menu comprising the plurality of healthcare plan choices as having been determined again based at least in part on the one or more medical parameters, and receiving the indication of the respective plan selection button having been selected after causing the menu to be again provided for display on the user interface component.

11. The method of claim 10, wherein the one or more medical parameters comprises an identification of one or more prescription medicines, and wherein determining the plurality of healthcare plan choices comprises:

identifying a pharmacy having a minimum total cost for the one or more prescription medicines and determining the plurality of healthcare plan choices based at least in part on the pharmacy having the minimum total cost for the one or more prescription medicines.

12. The method of claim 11, wherein identifying the pharmacy having the minimum total cost for the one or more prescription medicines comprises making an application programming interface call to a pharmaceutical cost data provider.

13. The method of claim 12, wherein the one or more medical parameters comprises a further identification of one or more preferred pharmacies, and wherein the pharmacy having the minimum total cost for the one or more prescription medicines differs from the one or more preferred pharmacies.

14. The method of claim 11, wherein the one or more prescription medicines comprises a first medicine that has at least one generic alternative, and wherein the minimum total cost is based at least in part on the at least one generic alternative.

15. A system comprising at least one processor and at least one non-transitory memory comprising computer executable instructions that when executed by the at least one processor, cause the at least one processor to carry out actions comprising:

causing a first modal dialog to be provided for display on a user interface component, the first modal dialog comprising a first prompt, the first prompt requesting one or more geographical location parameters;

responsive to receiving the one or more geographical location parameters, causing a second modal dialog to be provided for display on the user interface component, the second modal dialog comprising a second prompt and a bypass button, the second prompt presenting a user with an option of providing one or more medical parameters or selecting the bypass button operable to bypass the option of providing of the one or more medical parameters;

wherein the second prompt further comprises an add your pharmacy button and an add your doctor button;

wherein the one or more medical parameters comprise a plan wall;

updating the plan wall based on a county and a zip code by a web services call to a data provider;

wherein the plan wall comprises one or more tabs, the one or more tabs comprising options including: advantage prescription drug plans, prescription drug plans, advantage plans, and supplement plans;

causing display of the plan wall;

receiving at least one selection of the options;

responsive to receiving an indication of the bypass button having been selected, determining a plurality of healthcare plan choices based at least in part on the one or more geographical location parameters and the at least one selection from the options and causing a menu to be provided for display on the user interface component, the menu comprising the plurality of healthcare plan choices and a navigate-back button operable to allow the user to navigate back to the second modal dialog;

responsive to receiving an additional indication of the navigate-back button having been selected, causing the second modal dialog to be again provided for display on the user interface component;

responsive to receiving the one or more medical parameters, determining again the plurality of healthcare plan choices based at least in part on the one or more medical parameters, and causing the menu to be again provided for display on the user interface component, the menu comprising the plurality of healthcare plan choices as having been determined again based at least in part on the one or more medical parameters;

responsive to receiving a further indication of a respective plan selection button having been selected, causing a third modal dialog to be provided for display on the user interface component, the third modal dialog comprising information for enrolling in a respective one of the plurality of healthcare plan choices corresponding to the respective plan selection button;

determining pharmacies in an area associated with the one or more geographical location parameters;

filtering the pharmacies to only those that provide the one or more medical parameters;

causing display of a list of the pharmacies that provide the one or more medical parameters within the area;

receiving, by the user interface component and from the user, input of at least one preferred pharmacy that is not on the list of the pharmacies; and adding the at least one preferred pharmacy to the list of the pharmacies.

16. The system of claim 15, wherein the one or more geographical location parameters comprises the zip code and the county.

17. The system of claim 15 wherein the one or more medical parameters comprises an identification of one or more prescription medicines, and wherein determining the plurality of healthcare plan choices comprises:

identifying a pharmacy having a minimum total cost for the one or more prescription medicines and determining the plurality of healthcare plan choices based at least in part on the pharmacy having the minimum total cost for the one or more prescription medicines.

18. The system of claim 17, wherein the one or more medical parameters comprises a further identification of one or more preferred pharmacies, and wherein the pharmacy having the minimum total cost for the one or more prescription medicines differs from the one or more preferred pharmacies.

19. The system of claim 17, wherein identifying the pharmacy having the minimum total cost for the one or more prescription medicines comprises making an application programming interface call to a pharmaceutical cost data provider.

20. The system of claim 19, wherein the one or more prescription medicines comprises a first medicine that has at least one generic alternative, and wherein the minimum total cost is based at least in part on the at least one generic alternative.

* * * * *